United States Patent [19]

Rinehart

[11] Patent Number: 4,950,649

[45] Date of Patent: Aug. 21, 1990

[54] DIDEMNINS AND NORDIDEMNINS

[75] Inventor: Kenneth L. Rinehart, Urbana, Ill.

[73] Assignee: University of Illinois, Urbana, Ill.

[21] Appl. No.: 137,484

[22] Filed: Dec. 23, 1987

Related U.S. Application Data

[60] Continuation-in-part of Ser. No. 894,442, Jul. 31, 1986, abandoned, and Ser. No. 457,615, Jan. 13, 1983, abandoned, which is a continuation-in-part of Ser. No. 299,897, Sep. 8, 1981, abandoned, which is a continuation-in-part of Ser. No. 186,932, Sep. 12, 1980, abandoned, said Ser. No. 894,442, is a continuation of Ser. No. 663,824, Oct. 22, 1984, abandoned, which is a continuation of Ser. No. 449,296, Dec. 13, 1982, abandoned, which is a continuation of Ser. No. 299,894, Sep. 8, 1981, abandoned, which is a division of Ser. No. 217,768, Dec. 18, 1980, abandoned, which is a continuation-in-part of Ser. No. 186,932, Sep. 12, 1980, abandoned.

[51] Int. Cl.$^5$ .............................................. A61K 37/00
[52] U.S. Cl. ...................................................... 514/10
[58] Field of Search .......................................... 514/10

[56] References Cited

PUBLICATIONS

Morishima et al., Jr. of Antibiotics, vol. XXIII, No. 5, May 1970, pp. 263–265.
Dorr et al., Clinical Pharmacology (Adult & Pediatric) (Proceedings of Amer. Soc. Clin. Oncol., vol. 5, Mar. 1986), p. 39 (No. 151).
Stewart et al., Clinical Pharmacology (Adult & Pediatric) (Proceedings of Amer. Soc. Clin. Oncol., vol. 5, Mar. 1986), p. 33 (No. 128).
Jiang et al., Cancer Chemotherapy & Pharmacology, 1983, vol. 11, pp. 1–4.

Primary Examiner—Jerome D. Goldberg
Attorney, Agent, or Firm—Ruth H. Newtson; Donald L. Corneglio

[57] ABSTRACT

Novel antibiotics didemnins A, B and C (didemnins), and nordidemnins A, B and C (nordidemnins) which can be obtained from a marine organism. These antibiotics are active against a variety of DNA and RNA viruses; thus, they can be used in various environments to control or eradicate these viruses. Further, these antibiotics can be used to treat animals and humans hosting acute myelocytic leukemia and acute lymphocytic leukemia.

1 Claim, 2 Drawing Sheets

DIDEMNINS AND NORDIDEMNINS

CROSS REFERENCE TO RELATED APPLICATIONS

This application is a continuation-in-part of copending application Ser. No. 457,615 filed Jan. 13, 1983, now abandoned which is a continuation in part of Ser. No. 299,897 filed Sept. 8, 1981, now abandoned, which is a continuation-in-part of Ser. No. 186,932 filed Sept. 12, 1980, now abandoned, and of copending application Ser. No. 894,442 filed July 31, 1986, now abandoned, which is a continuation of Ser. No. 663,824 filed Oct. 22, 1984, now abandoned, which is a continuation of Ser. No. 449,296 filed Dec. 13, 1982, now abandoned, which is a continuation of Ser. No. 299,894 filed Sept. 8, 1981, now abandoned, which is a division of Ser. No. 217,768 filed Dec. 18, 1980, now abandoned, which is a continuation-in-part of Ser. No. 186,932 filed Sept. 12, 1980, now abandoned.

BRIEF SUMMARY OF THE INVENTION

Novel antibiotics didemnin A, didemnin B, didemnin C, nordidemnin A, nordidemnin B, and nordidemnin C are extracted from a marine tunicate of the family Didemnidai, and tentatively identified as a Trididemnum sp. These antibiotics are active against DNA viruses, for example, herpes simples virus types 1 and 2, and vaccinia virus; RNA viruses, for example, coxsackie virus and equine rhinovirus; and B388 leukemia in mice. Thus these antibiotics can be used to treat infections in humans, animals and plants caused by these viruses and other DNA and RNA viruses. Didemnin A and didemnin B also inhibit L1210 mouse leukemia cells in vitro. Acid addition salts and acyl derivatives of the didemnins can be made and used for the same biological purposes are the parent compounds.

DETAILED DESCRIPTION OF THE INVENTION

Figure 1:
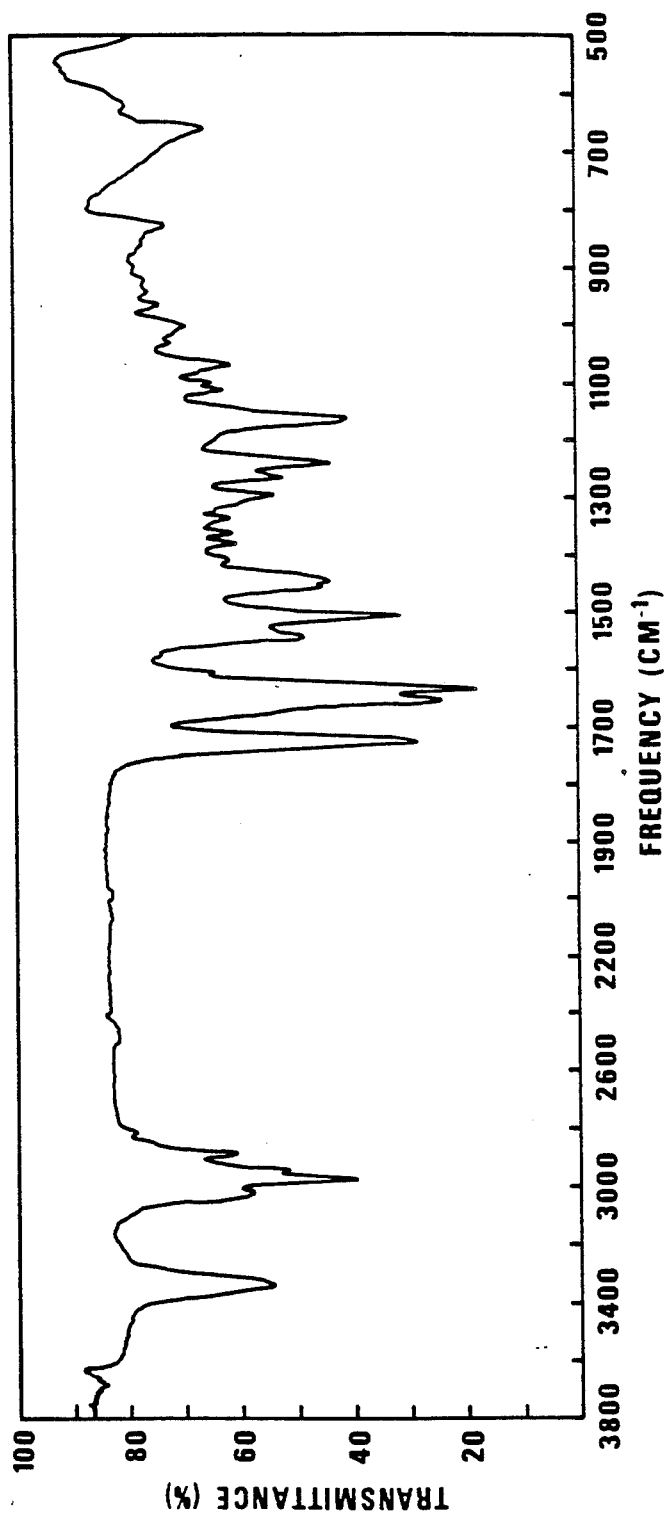

The organism from which didemnins and nordidemnins (A, B, and C) are extracted is a colonial marine tunicate of the family Didemnidae Trididemnum sp. These organisms are in the suborder Aplousobranchia of the order Enterogona of the class Ascidiacea of the subphylum Urochordata of the phylum Chordata. They can be readily obtained by scuba techniques at depths of 10 to 100 feet where they encrust rocks, sponges, gorgonians, etc., in colony sizes up to 3 feet in diameter and ½ inch in thickness. They vary in color depending on location from green-white to purple-white to brown-white to orange-white.

Specific locations from which these organisms have been obtained are as follows:

(1) Southwest side of Long Gay, Lighthouse Reef, Belize, 17° 11.8' N by 87° 36.5' W at a depth of 50 to 100 feet; (2) Rada el Cove, Isla San Andres, Colombia, 12° 31'46" N by 81° 44'5" W at 25 to 33 feet; (3) Panancar Reef, Isla de Cozumel, Mexico, 20° 18.2' N by 87° 2.5' W at 60 to 100 feet; (4) on the west side of the southern tip of Turneffe Island, Belize, 17° 11.3' N by 87° 55.6' W at 50 to 75 feet; (5) Punta Oeste, Coxen's Hole Harbor, Isla Roatan, Honduras, 16° 15' N by 86° 38' W at 10 to 70 feet; (6) on the leeward side of the western-most Holandes Cay, Isla San Blas, Panama, 9° 35.6' N by 78° 47' W at 60 feet.

A variety of methods can be used to isolate and purify the didemnins and nordidemnins from samples of the tunicate organism, for example, solvent extraction, partition chromatography, silica gel chromatography, liquid-liquid distribution in a Craig apparatus, adsorption on resins, and crystallization from solvents.

The following examples describe preferred processes, but are not to be construed as limiting.

EXAMPLE 1

Tunicate sample AHCE #614 was collected on the southwest side of Long Cay, Lighthouse Reef, Belize, 17° 11.8' N by 87° 36.5' W at a depth of 50 to 100 feet. The sample was placed in isopropanol and stored at −10° C. until it was extracted by the following procedure.

500 Grams of tunicate were homogenized in a Waring blender with a total of 2.4 liters of 3:1 MeOH:toluene and the residue was filtered with suction to give a dark olive green solution. 500 Ml of the aqueous isopropanol from the storage container was evaporated down ~40 ml of a mostly aqueous oily solution. This material was suspended in 400 ml of 3:1 methanol:toluene and combined with the 2.4 liters above.

The resulting dark green solution was partitioned versus 1400 ml of 1N $NaNO_3$ solution to give an aqueous phase and a toluene phase. The aqueous phase was extracted with chloroform (1×500 ml, 1×300 ml, 2×250 ml and 1×100 ml) to give a cloudy grass green chloroform solution which was evaporated under reduced pressure, taken up in dry $CHCl_3$, and filtered to remove salt. Evaporation of the chloroform yielded 878 mg of a dark green flaky solid.

108 Mg of this material was loaded onto a silica gel (Brinkmann, particle size 0.05–0.2 mm) column of dimensions 1.7 cm×46 cm, which was packed in chloroform. The column was eluted in step gradient fashion with 150 ml $CHCl_3$, 150 ml $CHCl_3$:MeOH, 99:1; 150 ml $CHCl_3$:MeOH, 97:3; and 250 ml $CHCl_3$:MeOH, 95:5. Three-ml fractions were collected, and the content of each fraction was evaluated by thin-layer chromatography developed with 9:1 $CHCl_3$:MeOH.

Relatively impure didemnin C (Rf 0.66–0.72) was obtained as an oil in trace amounts as the first major non-pigment to elute. It was contained in the last 30 ml of the 3% methanol in chloroform wash. Essentially pure didemnin C can be obtained by use of preparative thin-layer chromatography, as described for preparing didemnin A, below, Essentially pure didemnin B (Rf 0.59–0.64) was obtained as a yellow-white amorphous solid (6.1 mg). In most cases, didemnin B was already pure enough (by TLC) for data accumulation and testing. Didemnin A (Rf 0.46–0.52) was obtained as a greenish-white solid (34.7 mg) containing substantial impurities of both higher and lower Rf. Didemnins B and A were contained in the first 100 ml of the 5% methanol in chloroform wash. When as essentially pure sample was desired (for mass spectroscopy, etc.), didemnin A was purified by preparative thin-layer chromatography on 0.25 mm TLC plates employing 9:1 $CHCl_3$:MeOH as the eluent. In many cases, the best fractions of didemnin A collected from later columns had fewer impurities, which allowed immediate use for reaction and spectral data accumulation.

EXAMPLE 2

Salts of Didemnins

Since the didemnins are weakly basic, they form salts with mineral acids such as HCl, $H_2SO_4$, $H_3PO_4$, and the like. Such salts can be prepared by suspending the didemnins in water, adding a dilute acid until the pH of the solution is about 3 to 4, and freeze-drying the solution to provide a dried residue of the didemnin salt. Salts of the didemnins can be used for the same biological purposes as the parent compounds.

EXAMPLE 3

Derivatives of Didemnins

The didemnins have free amino and hydroxyl groups available for derivatization. Thus, acyl amides and esters of the didemnins can be prepared by methods well known to those skilled in the art. Acyl derivatives of the didemnins can be used for the same biological purposes as the parent compounds.

Acids which can be used in the acylation of a didemnin include (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarbon carboxylic acids as given above which are substituted by one or more of halogen, nitro, hydroxy, keto, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are:
mono-, di-, and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
skikimic acid;
2-nitro-1-methyl-cyclobutanecarboxylic acid;
1,2,3,4,5,6-hexsachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclogexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-diemthylcyclohexanecarboxylic acid;
homogentisic acid, o-, m- and p-chlorobenzoic acid;
anisic acid;
salicylic acid;
p-hydroxybenzoic acid;
β-resorcyclic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
malic acid;
citric acid;
isocitric acid;
6-methylsalicyclic acid;
mandelic acid;
levulinic acid;
pyruvic acid;
glycine;
alamine;
valine;
isoleucine;
leucine;
phenylalanine;
proline;
serine;
threonine;
tyrosine;
hydroxyproline;
ornithine;
lysine;
arginine;
histidine;
hydroxylysine;
phenylglycine;
p-aminobenzoic acid;
m-aminobenzoic acid;
anthranilic acid;
aspartic acid;
glutamic acid;
aminoadipic acid;
glutamine;
asparagine;
and the like.

EXAMPLE 4

Isolation of Nordidemnins

Nordidemnins (A, B and C) are minor homologs of each didemnin in which norstatine replaces statine. The nordidemnins can be separated from the didemnins and isolated in essentially pure form by reverse phase high pressure liquid chromatography, monitoring the N,O-dimethyltyrosine chromophore by ultraviolet spectroscopy at 275 nm. Usable solvent systems for these separations include combinations of methanol, water and triethylamine; methanol, water and 2-propanol; or ethanol, water, and 2-propanol. Nordidemnins A, B & C give molecular ions at m/z 928, 1097, and 1000, respectively. Hydrolysis in acid, derivatization and gas chromatography/mass spectrometry identified norstatine as replacing statine. Salts and derivatives of the nordidemnins can be made in accord with the procedures disclosed in Examples 2 and 3. These compounds, as well as the nordidemnins themselves, can be used for the same biological purposes as disclosed for the didemnins.

CHARACTERIZATION OF DIDEMNINS

Solubilities

Didemnins A, B and C are soluble in methanol, ethanol, isopropanol, dioxane, ethyl acetate, and chloroform. They are only sparingly soluble in toluene and insoluble in water. Nordidenmins A, B and C have a similar solubility pattern.

Acid Hydrolysis of Didemnins

The didemnin samples were hydrolyzed in 6N HCl at 110° C. for 24 hours. The resulting amino acids were identified by field desorption mass spectrometry (FDMS) of the mixture, as well as by gas chromatography (GC)/MS of the amino acids' trifluoroacetyl n-butyl ester derivatives. They were also quantitated by GC, and their identities confirmed by coinjection with derivatives of authentic samples.

Didemnin A contains a mole each of leucine; N-methylleucine, threonine; proline; N,O-dimethyltyrosine; and statine [see H. Morishima et al., Journal of Antibiotics 23:263 (1970) for a description of statine (from pepstatin)]. Statine was assigned as the threo isomer by its co-elution with the synthetic R,S-isomer, while gas chromatography on an optically active column indicated Leu, MeLeu, and $Me_2Tyr$ to have the L-configuration.

Didemnin B contains a mole of each of the above six amino acids plus a mole of lactic acid and an additional mole of proline. Didemnin C contains a mole of each of the above six amino acids plus a mole of lactic acid, in addition to the above amino acids, each didemnin contains a hydroxy-isovalerylpropionyl group.

The order of linkage of these seven units was established by the fragment ions identified in high resolution electron impact mass spectra.

Each of the didemnins (A, B, C) is accompanied by a minor but varying amount of a homolog. The nature of the homology was clarified by the observation that GC traces of the dervatized amino acids always contain minor amounts of an amino acid identified by GC/MS as a homolog of statine, for which we propose the name norstatine [$(CH_3)_2CHCHNH_2CHOHCH_2COOH$]. The homologous peptides can then properly be designated as nordidemnins A, B and C, in which norstatine replaces the statine unit of each didemnin.

Mass Spectra

Didemnin A has the following mass spectral peaks: a molecular ion at 942.5678 ($C_{49}H_{78}N_6O_{12}$) and fragments at m/z 886, 843, 800, 756, 611, 583, 557, 523, 501, 499, 480, 455, 401, 383, 356, 313, 310, 298, 288, 262, 210, 183, 178, 154, 139, 134, 128, 122, 121, 100.

The field desorption mass spectrum of didemnin B gines an M+H ion at 1112.6442 ($C_{57}H_{90}N_7O_{15}$). The electron impact mass spectrum of didemnin B contains ions at m/z 942, 924, 913, 886, 844, 843, 797, 756, 611, 593, 557, 523, 425, 396, 383, 313, 307, 288, 262, 224, 210, 183, 154, 121, 100.

The field desorption mass spectrum of didemnin C contains an M+H ion at 1014.5873 ($C_{52}H_{82}N_6O_{14}$). in addition, the mass spectrum of didemnin C obtained by electron impact gives ions at m/z 958, 887, 859, 842, 693, 675, 578, 547, 536, 494, 368, 283, 262, 237, 224, 200, 172, 154, 121, 100. The minor homolog of didemnin C gives an M+H ion at 1000.5714 ($C_{51}H_{80}N_6O_{14}$). Its electron impact mass spectrum contains peaks at m/z 944, 873, 845 and 828 indicative of the homology.

NMR Spectra

Didemnin A had the following proton NMR peaks, in ppm from tetramethylsilane: 8.3, 7.8, 7.5, 7.1, 6.9, 5.2, 5.0, 4.9, 4.8, 4.6, 4.2, 4.1, 4.0, 3.8, 3.7, 3.6, 3.4, 3.2, 3.1, 2.9, 2.6 (singlet methyl), 2.6 (doublet of doublets), 2.4 (singlet methyl), 2.4 (multiplet), 2.1, 1.8, 1.6, 1.4, 1.35, 1.30, 1.2, 0.9, (several overlapping methyl doublets).

Didemnin B had the following proton NMR peaks, in ppm from tetramethylsilane: 8.0, 7.8, 7.4, 7.2, 7.0, 5.5, 5.4, 5.3, 4.9, 4.8, 4.6, 4.5, 4.4, 4.2, 3.9, 3.8, 3.5, 3.4, 3.3, (doublet), 3.3 (singlet methyl), 3.1, 2.8, 2.7 (singlet methyl), 2.5, 2.3, 2.1, 1.9, 1.7, 1.5, 1.4, 1.3, 1.0 (several overlapping methyl doublets).

Didemnin C had the following proton NMR peaks, in ppm from tetramethylsilane: 7.7, 7.4, 7.2, 7.0, 5.2, 5.0, 4.8, 4.5, 4.2, 4.0, 3.7, 3.5, 3.5, 3.1, 3.0, 2.9, 2.8 (singlet methyl), 2.4 (singlet methyl), 2.3, 2.2, 2.1, 1.8, 1.5, 1.4-1.25, 1.1-0.8 (several overlapping methyls).

Didemnin A had the following $^{13}C$-NMR signals, relative to tetramethylsilane in $CDCl_3$: 205.1, 175.3, 1723.3, 171.4, 170.4, 169.9, 169.6, 168.6, 158.7, 130.4 (2 carbons), 129.9, 114.2 (2 carbons), 81.5, 71.1, 67.6, 66.2, 63.2, 57.4, 55.3, 54.7, 49.9, 49.5, 47.1, 42.5, 41.3, 38.6 (2 carbons), 35.4, 34.2, 34.0, 31.2, 27.9, 27.0, 25.1 (2 carbons), 24.9, 23.7, 22.9, 22.3, 21.0, 18.7, 16.9, 15.4, 14.9 (2 carbons), 11.7.

Didemnin B has the following $^{13}C$-NMR signals relative to tetramethyl silane in $CDCl_3$: 204.9, 174.0, 172.9, 172.4, 171.8, 171.3, 170.6, 169.7, 169.4, 168.4, 158.7, 130.3 (2 carbons) 130.1, 114.2 (2 carbons), 81.5, 70.5, 68.0, 66.5, 66.0, 57.7, 57.2, 56.7, 55.5, 55.3, 54.9, 49.6 (2 carbons), 47.0 (2 carbons), 41.4, 38.9, 38.7, 36.2, 34.0 (2 carbons), 31.3 (2 carbons), 28.4, 27.9, 27.2, 26.0, 24.9 (3 carbons) 23.8, 23.4, 21.4, 21.0, 20.3, 18.6, 16.9, 16.3, 15.2, 14.7, 11.7

Infrared Spectra

The didemnins were dissolved in chloroform and examined in a Beckman IR-12 double beam spectrophotometer vs. a chloroform reference.

The spectrum of didemnin A is shown in FIG. 1. Peaks are observed at the following wavelengths:

| Band Frequency (Wave Number $cm^{-1}$) | Intensity (% T) |
| --- | --- |
| 3680 | 84 |
| 3600 | 82 sh |
| 3520 | 70 |
| 3340 | 54 |
| 3020 | 57 |
| 2970 | 39 |
| 2940 | 51 |
| 2880 | 60 |
| 2810 | 78 |
| 2460 | 82 |
| 1725 | 27.5 |
| 1650 | 23 |

-continued

| Band Frequency (Wave Number cm$^{-1}$) | Intensity (% T) |
|---|---|
| 1630 | 17 |
| 1605 | 64 |
| 1540 | 48 |
| 1505 | 31 |
| 1455 | 45 |
| 1445 | 43 |
| 1405 | 61 |
| 1380 | 59 |
| 1360 | 60 |
| 1335 | 60.5 |
| 1325 | 64 |
| 1310 | 60 sh |
| 1295 | 53 |
| 1265 | 51 |
| 1240 | 43 |
| 1195 | 63 sh |
| 1160 | 40 |
| 1110 | 62 |
| 1100 | 63.5 |
| 1080 | 66 sh |
| 1065 | 60 |
| 1030 | 71 |
| 1000 | 68 |
| 965 | 73 |
| 940 | 75 |
| 920 | 76 |
| 900 | 78 |
| 825 | 72 |
| 660 | 65 |
| 620 | 79 | sh = shoulder

Figure 2:
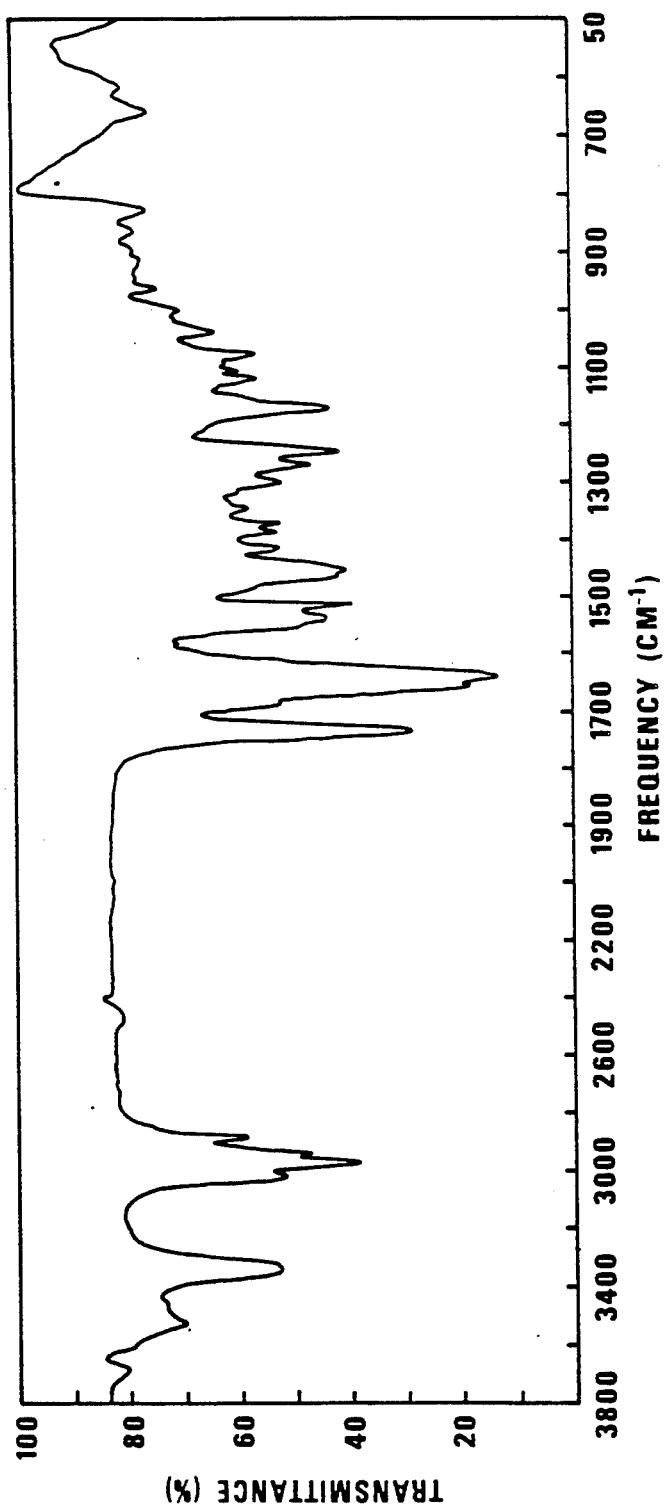

The spectrum of didemnin B is shown in FIG. 2. Peaks are observed at the following wavelengths:

| Band Frequency (Wave Number cm$^{-1}$) | Intensity (% T) |
|---|---|
| 3680 | 80 |
| 3600 | 79 |
| 3340 | 52.5 |
| 3020 | 51.5 |
| 2970 | 38 |
| 2940 | 47 |
| 2880 | 58 |
| 2460 | 81 |
| 1725 | 28 |
| 1650 | 17 |
| 1640 | 13 |
| 1630 | 15 sh |
| 1605 | 51 sh |
| 1540 | 44 |
| 1514 | 38.5 |
| 1465 | 41 |
| 1455 | 40 |
| 1415 | 52 |
| 1390 | 52.5 |
| 1370 | 52 |
| 1345 | 57.5 |
| 1300 | 51 |
| 1270 | 46 |
| 1250 | 40.5 |
| 1170 | 42 |
| 1120 | 56 |
| 1105 | 59 |
| 1075 | 56 |
| 1040 | 63.5 |
| 1000 | 70 |
| 965 | 73.5 |
| 940 | 77 |
| 910 | 76.5 |
| 900 | 78 |
| 865 | 78 |
| 830 | 76 |
| 660 | 75 |

-continued

| Band Frequency (Wave Number cm$^{-1}$) | Intensity (% T) |
|---|---|
| 615 | 80 | sh = shoulder

The infrared absorption spectrum for didemnin C when pressed into a KBr disc is as follows:

| Band Frequency | Intensity | Type |
|---|---|---|
| 3672.9 | 73 | SH |
| 3562.9 | 50 | SH |
| 3501.2 | 40 | SH |
| 3479.0 | 38 | SH |
| 3421.1 | 35 | SH |
| 3339.1 | 22 | BRD |
| 3214.7 | 56 | SH |
| 3065.2 | 60 | BRD |
| 3031.4 | 59 | BRD |
| 2962.0 | 12 | AVG |
| 2935.0 | 19 | AVG |
| 2875.2 | 33 | AVG |
| 2794.2 | 71 | SH |
| 2499.0 | 79 | BRD |
| 2063.1 | 80 | BRD |
| 1733.2 | 11 | AVG |
| 1663.8 | 6 | AVG |
| 1639.6 | 3 | AVG |
| 1583.7 | 49 | AVG |
| 1544.2 | 22 | AVG |
| 1514.3 | 13 | SHP |
| 1488.2 | 33 | AVG |
| 1453.5 | 16 | AVG |
| 1413.0 | 31 | AVG |
| 1400.4 | 33 | BRD |
| 1386.0 | 25 | AVG |
| 1369.6 | 29 | AVG |
| 1342.6 | 32 | AVG |
| 1318.5 | 20 | AVG |
| 1305.0 | 24 | AVG |
| 1261.5 | 11 | AVG |
| 1250.0 | 14 | AVG |
| 1220.1 | 21 | AVG |
| 1169.0 | 14 | AVG |
| 1116.9 | 21 | SH |
| 1106.3 | 16 | AVG |
| 1092.8 | 17 | AVG |
| 1077.3 | 16 | AVG |
| 1033.9 | 19 | AVG |
| 1022.3 | 20 | SH |
| 966.4 | 54 | AVG |
| 938.4 | 63 | AVG |
| 924.0 | 63 | AVG |
| 862.2 | 58 | AVG |
| 802.4 | 20 | AVG |
| 755.2 | 60 | AVG |
| 720.4 | 57 | AVG |
| 704.1 | 58 | AVG |
| 650.0 | 54 | AVG |
| 615.3 | 53 | AVG |

Band Frequency in wavenumbers (cm$^{-1}$)
Intensity in percent to transmittance (% T)
Data type in local peak region: BRD = Broad, AVG = Average, SH = Shoulder This peak list is unedited

| % T | Frequency |
|---|---|
| 3 | 1639.5 |
| 6 | 1663.7 |
| 11 | 1733.1 |
| 11 | 1261.5 |
| 12 | 2962.0 |
| 13 | 1514.2 |
| 14 | 1250.0 |
| 14 | 1169.0 |
| 16 | 1453.5 |
| 16 | 1106.2 |

-continued

| % T | Frequency |
|---|---|
| 16 | 1077.2 |
| 17 | 1092.7 |
| 19 | 2935.0 |
| 19 | 1033.8 |
| 20 | 1318.5 |
| 20 | 1022.2 |
| 20 | 802.3 |
| 21 | 1220.0 |
| 21 | 1116.8 |
| 22 | 3339.0 |
| 22 | 1544.1 |
| 24 | 1305.0 |
| 25 | 1386.0 |
| 29 | 1369.5 |
| 31 | 1413.0 |

The IR spectra for nordidemnin A, B and C are essentially the same as for didenmin A, B and C, respectively.

ANTIVIRAL ACTIVITY

The antiviral activities of didemnins A, B and C are shown in the following table. The test method is as follows:

Costar 96 well trays were seeded with 0.2 ml cell suspension and incubated at 37° for 24 hours. The medium was removed and the wells were treated with serial 2-fold dilutions of drug (150–1.5 μm/ml) in 0.05 ml. Diluted virus (0.05 ml) or medium (BME-3% fbs) was added to each well and the cultures were returned to 37°. After overnight incubation, the cells were stained with aqueous crystal violet (0.5%), and washed thoroughly. Drug concentrations resulting in 50% cell destruction ($ID_{50}$) were determined visually for those cultures infected with virus (antiviral) as well as those cultures serving as toxicity controls. Ratios are the cytotoxic concentration ÷ antiviral concentration.

The cells used for the herpes simplex virus (HSV) type 1 and type 2 were Vero. ML cells were used for the assays with coxsackie (COX) A21 and equine rhinovirus (ER).

| | $ID_{50}$ | | |
|---|---|---|---|
| | A | B | C |
| RNA Viruses | | | |
| Toxicity-ML cells | 25 | <1.5 | 6 |
| Antiviral-cox virus | 1.5 | <1.5 | <1.5 |
| Ratio | 17 | | >4 |
| Toxicity-ML cells | 25 | <1.5 | 6 |
| Antiviral-ER virus | 1.5 | <1.5 | <1.5 |
| Ratio | 17 | | >4 |
| DNA Viruses | | | |
| Toxicity-Vero cells | 50 | 12 | 50 |
| Antiviral-HSV-1 virus | 3 | 1.5 | <1.5 |
| Ratio | 17 | 8 | >33 |
| Toxicity-Vero cells | 50 | 12 | 50 |
| Antiviral-HSV-2 virus | 1.5 | 1.5 | <1.5 |
| Ratio | 33 | 8 | >33 |

ANTILEUKEMIA ACTIVITY

Didemnins A and B inhibit the growth of L1210 mouse leukemia cells in vitro as shown in the following table. The L1210 tube dilution assay is described in detail in a publication by L. H. Li, et al., Cancer Research 39:4816 (1979). $ID_{50}$ and $ID_{90}$ refer to the concentration of didemnins needed to inhibit cell growth by 50 and 90 percent, respectively.

| L1210 Tube Dilution Assay | | |
|---|---|---|
| | $ID_{50}$ μg/ml | $ID_{90}$ μg/ml |
| Didemnin A | 0.019 | 0.058 |
| Didemnin B | 0.0018 | 0.0059 |

Didemnins A and B were also active in vivo against P388 leukemia in mice. The P388 mouse leudemia test is described in detail in a publication by G. L. Neil, et al., Cancer Treatment Reports 63, 1971–1978 (1979). The results of two P388 mouse lekemia tests using different dosage schedules is shown below.

| In Vivo Testing of Didemnins Against P388 Leukemia | | | | |
|---|---|---|---|---|
| Compound[a] | Dose (μg/kg/ injection) | Median Survival Time[b] (day) | T/C (%) | Weight Change (g) |
| Didemnin A | 63 | 10.7 | 104 | +0.9 |
| | 125 | 11.9 | 115 | +1.4 |
| | 250 | 12.2 | 119 | +1.0 |
| | 500 | 13.2 | 129 | +0.9 |
| | 1000 | 16.2 | 158 | +0.3 |
| | 2000 | 16.0 | 155 | −0.2 |
| Didemnin B | 63 | 14.8 | 143 | +0.1 |
| | 125 | 14.0 | 136 | −0.6 |
| | 250 | 14.2 | 138 | −2.2 |
| | 500 | T[c] | T | −3.4 |
| | 1000 | T | T | T |
| | 2000 | T | T | T |

[a]Schedule of Injection: daily intraperitoneal injection for 9 days following tumor implantation.
[b]Median survival time of control animals = 10.3 days.
[c]Toxic.

| Compound[a] | Dose (μg/kg/ injection) | Median Survival Time[b] (day) | T/C (%) | Weight Change (g) |
|---|---|---|---|---|
| Didemnin A | 250 | 11.1 | 109 | +1.7 |
| | 500 | 12.1 | 118 | +1.6 |
| | 1000 | 12.1 | 118 | +1.8 |
| | 2000 | 12.4 | 121 | +2.0 |
| | 4000 | 13.3 | 130 | +1.3 |
| | 8000 | 14.3 | 140 | +0.8 |
| Didemnin B | 30 | 12.8 | 125 | +1.6 |
| | 60 | 14.3 | 140 | +1.2 |
| | 120 | 15.0 | 147 | +0.2 |
| | 250 | 16.0 | 157 | −0.5 |
| | 500 | 18.0 | 176 | −1.7 |
| | 1000 | 20.3 | 199 | −3.8 |

[a]Schedule of injection: Intraperitoneal injection on Day 1, 5, and 9, following Tumor inoculation.
[b]Median survival time of Control (no drug) animals: 10.2 days.

The administration of didemnins A, B or C and nor-didemnins A, B or C is useful prophylactically and therapeutically for treating neoplastic diseases and viral infections. For example, pharmaceutical compositions containing the active ingredients are useful in prophylactic or therapeutic treatment of humans and animals infected or likely to be infected with viruses, e.g., hepatitis virus, rubella, rubeola, influenza, encephalitis viruses (i.e., arboviruses such as western or eastern equine encephalitis virus, Semliki Forest virus), herpes viruses (types 1 or 2 herpes simplex virus, cytomegalovirus, varicella-zoster and infectious bovine rhinotracheitis virus), rabies, enteroviruses (picornaviruses, echoviruses, coxsackie viruses), parainfluenza viruses, respiratory syncytial virus, sendai virus, poliomyelitis viruses, yellow fever, Epstein-Barr virus (infectious mononucleosis), small pox, Dengue virus, common cold virus (rhinoviruses, coronaviruses, etc.), adenoviruses, polyomaviruses, papovaviruses, RNA-tumor viruses (e.g., feline leukemia virus, avian leukosis virus, avian sarcoma virsuses), B virus, aleutians disease of mink, arena viruses, blue tongue virus of sheep, bovine viral diarrhea-mucosal disease virus, canine distemper virus, canine hepatitis virus, canine herpesvirus, equine abortion virus, infectious equine anemia virus, fowl pox virus, hog cholera virus, Marek's disease, mink enteritis virus, Newcastle disease virus, porcine enterovirus, pseudorabies virus, foot and mouth disease virus, reoviruses, and all other viruses or diseases of viral origin (for example, slowly progressing diseases that may be of viral origin such as multiplesclerosis) that are sensitive to the antiviral action of the didemnins or nordidemnins.

The compounds of the subject invention also can be used to treat animals or humans hosting acute myelocytic leukemia and acute lymphocytic leukemia.

The dosage administered will be dependent upon the identity of the viral infection of neoplastic disease, the type of host involved, its age, health, weight, kind of concurrent treatment, if any, frequency of treatment and therapeutic ratio.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally, 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powder, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as in adjuvant to the filling operation, a lubricant such as a talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except than an active ingredient is suspended in the vehicle instead of being dissolved and sterilization cannot be accomplished by filtration. The active ingredient can be sterilized by exposure to ethylene oxide before suspending in the sterile vehicle, Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or by dry powder for insufflation.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like nontoxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as anti-viral can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

EXAMPLE 5

Hard-Gelatin Capsules

One thousand two-piece hard gelatin capsules for oral use, each capsule containing 100 mg of a didemnin or a nordidemnin, are prepared from the following types and amounts of ingredients:

| a didemnin, micronized | 100 gm |
| Lactose | 100 gm |
| Corn Starch | 20 gm |
| Talc | 20 gm |
| Magnesium stearate | 2 gm |

The didemnin finely divided by means of an air micronizer, is added to the other finely powdered ingredients, mixed thoroughly and then encapsulated in the usual manner.

The foregoing capsules are useful for preventing or treating viral infection by the oral administration of one or two capsules one to four times a day.

Using the procedure above, capsules are similarly prepared containing didemnin or a nordidemnin in 50, 250 and 500 mg amounts by substituting 50 gm, 250 gm and 500 gm of didemnin for the 100 gm used above.

EXAMPLE 6

Soft Gelatin Capsules

One-piece soft gelatin capsules for oral use, each containing 250 mg of a didemnin or a nordidemnin (finely divided by means of an air micronizer), are prepared by first suspending the compound in 0.5 ml of corn oil to render the material capsulatable and then capsulating in the above manner.

The foregoing capsules are useful for preventing or treating viral infection by the oral administration of one or two capsules one to four times a day.

EXAMPLE 7

Tablets

One thousand tablets, each containing 500 mg of a didemnin or a nordidemnin are prepared from the following types and amounts of ingredients:

| A didemnin, micronized | 500 gm |
| Lactose | 75 gm |
| Corn starch | 50 gm |
| Magnesium stearate | 4 gm |
| Light liquid petrolatum | 5 gm |

The didemnin finely divided by means of an air micronizer, is added to the other ingredients and then thoroughly mixed and slugged. The slugs and broken down by forcing through a Number Sixteen screen. The resulting granules are then compressed into tablets, each tablet containing 500 mg of the didemnin.

The foregoing tablets are useful for preventing or treating viral infection by the oral administration of one or two tablets one to four times a day.

Using the procedure above, tablets are similarly prepared containing a didemnin or a nordidemnin in 250 mg and 100 mg amounts by substituting 250 gm and 10 gm of a didemnin for the 500 gm used above.

EXAMPLE 8

Oral Suspension

One thousand ml of an aqueous suspension for oral use, containing in each teaspoonful (5 ml) dose, 500 mg of a didemnin or a nordidemnin, is prepared from the following types and amounts of ingredients:

| A didemnin, micronized | 100 gm |
| Citric acid | 2 gm |
| Benzoic acid | 1 gm |
| Sucrose | 700 gm |
| Tragacanth | 5 gm |
| Lemon Oil | 2 gm |
| Deionized water, q.s. | 1000 ml. |

The citric acid, benzoic acid, sucrose, tragacanth and lemon oil are dispersed in sufficient water to make 850 mol of suspension. The didemnin, finely divided by means of an air micronizer, is stirred into the syrup until uniformly distributed. Sufficient water is added to make 1000 ml.

The composition so prepared is useful for preventing or creating viral infection at a dose of 1 tablespoonful (15 ml) three times a day.

EXAMPLE 9

A sterile aqueous suspension for parenteral injection, containing in 1 ml 300 mg of a didemnin is prepared from the following types and amounts of ingredients:

| A didemnin, micronized | 300 gm |
| Polysorbate 80 | 5 gm |

|   |   |
|---|---|
| Methylparaben | 2.5 gm |
| Propylparaben | 0.17 gm |
| Water for injection, q.s. | 1000 ml. |

All the ingredients, except the didemnin, are dissolved in the water and the solution sterilized by filtration. To the sterile solution is added the sterilized didemnin, finely divided by means of an air micronizer, and the final suspension is filled into sterile vials and the vials sealed.

The composition so prepared is useful for preventing or treating viral infection at a dose of 1 milliliter (1 M) three times a day.

EXAMPLE 10

Suppository, Rectal and Vaginal

One thousand suppositories, each weighing 2.5 gm and containing 150 mg of a didemnin or a nordidemnin are prepared from the following types and amounts of ingredients:

|   |   |
|---|---|
| A didemnin, micronized | 150 gm |
| Propylene glycol | 150 gm |
| Polyethylene glycol #4000, q.s. | 2,500 gm |

The didemnin is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for preventing or treating viral infection.

EXAMPLE 11

Intranasal Suspension

One thousand ml of a sterile aqueous suspension for intranasal instillation, containing in each ml 150 mg of a didemnin or a nordidemnin, is prepared from the following types and amounts of ingredients:

|   |   |
|---|---|
| A didemnin, micronized | 150 gm |
| Polysorbate 80 | 5 gm |
| Metnylparaben | 2.5 gm |
| Propylparaben | 0.17 gm |
| Deionized water, q.s. | 1000 ml. |

All the ingredients, except the didemnin, are dissolved in the water and the solution sterilized by filtration. To the sterile solution is added the sterilized didemnin, finely divided by means of an air micronizer, and the final suspension is aseptically filled into sterile containers.

The composition so prepared is useful for preventing or treating viral infection, by intranasal instillation of 0.2 to 0.5 ml given one to four times per day.

EXAMPLE 12

Animal Feed

One thousand grams of feed premix is prepared from the following types and amounts of ingredients:

|   |   |
|---|---|
| A didemnin (or nordidemnin) | 20 gm |
| Soybean meal | 400 gm |
| Fish meal | 400 gm |
| Wheat germ oil | 50 gm |
| Sorghum molasses | 130 gm |

The ingredients are mixed together and pressed into pellets.

The premix can be fed directly to laboratory animals, i.e., rats and mice, for preventing or treating viral infection.

For larger animals the premix can be added to the animal's regular feed in an amount calculated to give the desired dose of didemnin. For example, one part of premix is added to 2.5 parts of a cat's regular feed to provide the desired dose of 200 mg/kg/day for a cat of 2.5kg.

An active ingredient can also be present, as shown in Examples 12-15 in the undiluted pure form for use locally about the cutis, intranasally, pharyngolaryngeally, bronchially, broncholially or orally.

EXAMPLE 13

Powder

Five hundred grams of a didemnin or a nordidemnin in bulk form is finely divided by means of an air micronizer. The micronized powder is placed in a shaker-type container.

The foregoing composition is useful for preventing or treating viral infection, at localized sites by applying the powder one to four times per day.

EXAMPLE 14

Oral Powder

One thousand grams of a didemnin or a nordidemnin in bulk form is finely divided by means of an air micronizer. The micronized powder is divided into individual doses of 250 mg and packaged.

The foregoing powders are useful for preventing or treating viral infection, by the oral administration of one or two powders suspended in a glass of water, one to four times per day.

EXAMPLE 15

Insufflation

One thousand grams of a didemnin or a nordidemnin in bulk form is finely divided by means of an air micronizer.

The foregoing composition is useful for preventing or treating viral infection, by the inhalation of 30 to 75 mg one to four times per day.

EXAMPLE 16

Hard Gelatin Capsules

One thousand two-piece hard gelatin capsules for oral use, each capsule containing 100 mg of a didemnin or a nordidemnin.

The didemnin is finely divided by means of an air micronizer and encapsulated in the usual manner.

The foregoing capsules are useful for preventing or treating viral infection, by the oral administration or one or two capsules one to four times a day.

Using the procedure above, capsules are similarly prepared containing didemnin or a nordidemnin in 50, 250 and 500 mg amounts by substituting 50 gm, 250 gm and 500 gm of a didemnin for the 100 gm used above.

Data shows that the tentative structures for didemnin A, B and C can be shown as follows:

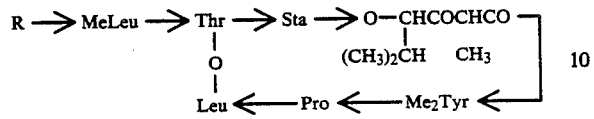

Didemnin A: R = H

Didemnin B: R = CH$_3$CHOHCO $\rightarrow$ Pro $\rightarrow$

Didemnin C: R = CH$_3$CHOHCO $\rightarrow$

Where

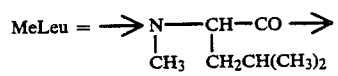

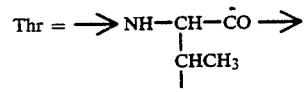

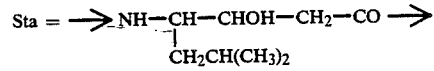

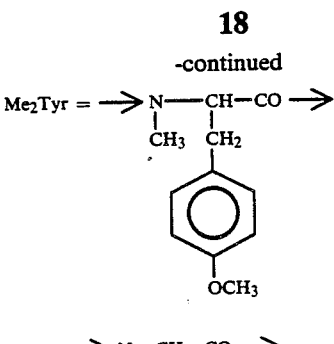

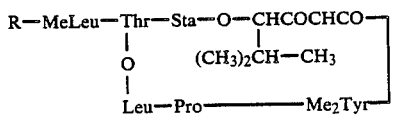

I claim:

1. A process for treating an animal or human host infected with an RNA or DNA virus which comprise the administration of an effective amount of a didemnin comprising the structural formula R—MeLeu—Thr—Sta—O—CHCOCHCO
                    |        |
                    O    (CH$_3$)$_2$CH—CH$_3$
                    |
                    Leu—Pro————Me$_2$Tyr where R is hydrogen, CH$_3$CHOHCO—Pro—, or CH$_3$CHOHCO—; or a pharmaceutically acceptable salt thereof, to said host whereby said virus is controlled or eradicated.

* * * * *

UNITED STATES PATENT AND TRADEMARK OFFICE
CERTIFICATE OF CORRECTION

PATENT NO. : 4,950,649
DATED : August 21, 1990
INVENTOR(S) : Rinehart

It is certified that error appears in the above-indentified patent and that said Letters Patent is hereby corrected as shown below:

Column 1, line 3, insert the following:

"This invention was made with Government support under Grant No. AI04769 awarded by the National Institutes of Health. The Government has certain rights in the invention."

Signed and Sealed this

Eighteenth Day of April, 1995

Attest:

BRUCE LEHMAN

*Commissioner of Patents and Trademarks*

*Attesting Officer*